(12) United States Patent
Rathjen

(10) Patent No.: US 12,036,151 B2
(45) Date of Patent: *Jul. 16, 2024

(54) APPARATUS FOR WORKING ON EYE TISSUE BY MEANS OF A PULSED LASER BEAM

(71) Applicant: Ziemer Ophthalmic Systems AG, Port (CH)

(72) Inventor: Christian Rathjen, Bremen (DE)

(73) Assignee: Ziemer Ophthalmic Systems AG, Port (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/127,291

(22) Filed: Mar. 28, 2023

(65) Prior Publication Data

US 2023/0248572 A1    Aug. 10, 2023

Related U.S. Application Data

(63) Continuation of application No. 17/150,407, filed on Jan. 15, 2021, now Pat. No. 11,642,245, which is a continuation of application No. 16/009,701, filed on Jun. 15, 2018, now Pat. No. 10,918,523.

(30) Foreign Application Priority Data

Jul. 13, 2017 (EP) .................... 17020300

(51) Int. Cl.
*A61F 9/008* (2006.01)
*A61B 17/00* (2006.01)
*A61B 18/20* (2006.01)

(52) U.S. Cl.
CPC ........ *A61F 9/0084* (2013.01); *A61F 9/00827* (2013.01); *A61F 9/00836* (2013.01); *A61B 2017/00154* (2013.01); *A61B 2018/20355* (2017.05); *A61B 2018/20359* (2017.05); *A61F 2009/00872* (2013.01); *A61F 2009/00897* (2013.01)

(58) Field of Classification Search
CPC ................ A61F 9/0084; A61F 9/00827; A61F 2009/00872; A61F 2009/00897
See application file for complete search history.

(56) References Cited

U.S. PATENT DOCUMENTS 5,274,492 A * 12/1993 Razzaghi ............. G02B 26/101
359/290
5,321,501 A * 6/1994 Swanson ............ G01B 9/02019
356/73.1

(Continued)

*Primary Examiner* — Eric D. Bertram
(74) *Attorney, Agent, or Firm* — Banner & Witcoff, Ltd.

(57) ABSTRACT

For the purposes of working on eye tissue, an ophthalmological apparatus comprises a laser source that is configured to produce a pulsed laser beam, a focusing optical unit that is configured to focus the pulsed laser beam into the eye tissue, and a scanner system for deflecting the pulsed laser beam onto work target points in the eye tissue. The scanner system is configured to guide the pulsed laser beam onto work target points along a scan line that extends across a work line at an alignment angle and to tilt the scan line depending on the work target point on the work line in such a way that the scan line extends substantially along an outer face of a lenticule to be cut in the eye tissue.

20 Claims, 8 Drawing Sheets

(56) References Cited

U.S. PATENT DOCUMENTS

| | | | | |
|---|---|---|---|---|
| 5,446,944 A * | 9/1995 | Coleman | | E05C 17/28 |
| | | | | 292/273 |
| 5,620,437 A * | 4/1997 | Sumiya | | A61F 9/008 |
| | | | | 606/5 |
| 5,784,148 A * | 7/1998 | Heacock | | A61B 3/1025 |
| | | | | 351/215 |
| 6,325,792 B1 * | 12/2001 | Swinger | | A61F 9/00834 |
| | | | | 606/4 |
| 6,758,564 B2 * | 7/2004 | Ferguson | | A61B 3/1025 |
| | | | | 351/221 |
| 7,220,255 B2 * | 5/2007 | Lai | | H01S 3/235 |
| | | | | 606/5 |
| 7,376,455 B2 * | 5/2008 | Crowley | | A61B 5/6852 |
| | | | | 600/475 |
| 7,621,637 B2 * | 11/2009 | Rathjen | | A61F 9/008 |
| | | | | 351/200 |
| 7,665,844 B2 * | 2/2010 | Chen | | G02B 26/0833 |
| | | | | 351/221 |
| 8,746,881 B2 * | 6/2014 | Rathjen | | A61F 9/008 |
| | | | | 351/208 |
| 9,138,349 B2 | 9/2015 | Wolfel et al. | | |
| 9,566,190 B2 * | 2/2017 | Rathjen | | A61B 18/18 |
| 9,849,033 B2 * | 12/2017 | Schuele | | A61F 9/00825 |
| 10,857,034 B2 * | 12/2020 | Rathjen | | A61F 9/00827 |
| 10,918,523 B2 * | 2/2021 | Rathjen | | A61F 9/00836 |
| 11,096,825 B2 * | 8/2021 | Rathjen | | A61F 9/00829 |
| 11,096,826 B2 * | 8/2021 | Rathjen | | A61F 9/0084 |
| 11,547,605 B2 * | 1/2023 | Rathjen | | A61F 9/00827 |
| 11,642,245 B2 * | 5/2023 | Rathjen | | A61F 9/0084 |
| | | | | 606/5 |
| 11,793,676 B2 * | 10/2023 | Rathjen | | A61F 9/00836 |
| 2005/0225721 A1 * | 10/2005 | Harris | | A61F 2/1645 |
| | | | | 351/200 |
| 2005/0267457 A1 * | 12/2005 | Hruschka | | A61B 18/20 |
| | | | | 607/101 |
| 2007/0110804 A1 * | 5/2007 | Royer | | A61L 27/20 |
| | | | | 514/35 |
| 2010/0137983 A1 * | 6/2010 | Culbertson | | A61F 2/1662 |
| | | | | 623/6.43 |
| 2012/0080586 A1 * | 4/2012 | Deisinger | | G01J 1/4257 |
| | | | | 250/252.1 |
| 2012/0150156 A1 * | 6/2012 | Wolfel | | A61F 9/008 |
| | | | | 606/4 |
| 2012/0150157 A1 * | 6/2012 | Wolfel | | A61F 9/00825 |
| | | | | 606/4 |
| 2012/0172854 A1 * | 7/2012 | Raymond | | A61F 9/008 |
| | | | | 606/5 |
| 2013/0158531 A1 * | 6/2013 | Goldshleger | | A61F 9/00825 |
| | | | | 606/6 |
| 2014/0364840 A1 * | 12/2014 | Donitzky | | A61F 9/008 |
| | | | | 606/4 |
| 2016/0073868 A1 * | 3/2016 | Raymond | | A61B 3/103 |
| | | | | 351/246 |
| 2016/0074125 A1 * | 3/2016 | Raymond | | A61F 9/00825 |
| | | | | 606/107 |
| 2016/0089270 A1 * | 3/2016 | Fu | | A61F 9/0084 |
| | | | | 606/5 |
| 2016/0150952 A1 * | 6/2016 | Raymond | | A61B 3/1015 |
| | | | | 351/205 |
| 2016/0302915 A1 * | 10/2016 | Sayegh | | A61F 9/007 |
| 2017/0027754 A1 * | 2/2017 | Muller | | A61F 9/00812 |
| 2018/0008461 A1 * | 1/2018 | Fu | | A61F 9/00829 |
| 2019/0099291 A1 * | 4/2019 | Herekar | | A61F 9/00802 |

* cited by examiner

APPARATUS FOR WORKING ON EYE TISSUE BY MEANS OF A PULSED LASER BEAM

CROSS REFERENCE TO RELATED APPLICATIONS

This application is a continuation application of U.S. application Ser. No. 17/150,407, filed Jan. 15, 2021, now U.S. Pat. No. 11,642,245, which is a continuation of U.S. application Ser. No. 16/009,701, filed Jun. 15, 2018, now U.S. Pat. No. 10,918,523, which claims priority to and the benefit of European Patent Application No. 17020300.4 filed on Jul. 13, 2017. The above-identified applications are incorporated by reference herein in their entireties.

FIELD OF TECHNOLOGY

The present disclosure relates to an ophthalmological apparatus for working on eye tissue by means of a pulsed laser beam. In particular, the present disclosure relates to an ophthalmological apparatus with a laser source for producing a pulsed laser beam, a focusing optical unit for focusing the pulsed laser beam into the eye tissue and a scanner system for guiding the pulsed laser beam onto a work target point in the eye tissue.

BACKGROUND

For the purposes of working on eye tissue by means of a laser beam, a work region is scanned by laser pulses by virtue of the pulsed laser beam being deflected in one or two scan directions by means of suitable scanner systems (deflection apparatuses). In general, movable mirrors are used to deflect the light beams and/or the laser pulses, for example femtosecond laser pulses, said movable mirrors being pivotable about one or two scan axes, for example by way of galvano scanners, piezo scanners, polygon scanners or resonance scanners.

U.S. Pat. No. 7,621,637 describes an apparatus for working on eye tissue, said apparatus having a base station with a laser source for producing laser pulses and a scanner, arranged in the base station, with movable deflection mirrors for deflecting the laser pulses in a scan direction. The deflected laser pulses are transferred via an optical relay system from the base station to an application head, the latter passing over a work region according to a scan pattern by means of a mechanically moved projection optical unit. In the application head, the deflection in the scan direction, which is much faster in comparison with the mechanical movement, is overlaid onto the mechanical movement of the projection optical unit and consequently onto the scan pattern thereof. A fast scanner system in the base station facilitates a fine movement of the laser pulses (micro-scan), which is overlaid on the scan pattern of the movable projection optical unit that covers a large work region, for example the entire eye.

Such known systems facilitate working on simple scan patterns, for example cutting a tissue flap, which, as a rule, is embodied as a large area piece with a simple edge geometry. In applications in which tissue cuts should not only be carried out in the work area that is aligned substantially horizontally on a common focal area but also be carried out with a vertical cut component with different focal heights, e.g. cuts that extend at an angle to the horizontal or vertical cuts, the vertical displacement of the projection optical unit or of a zoom system for a vertical change in the focus, and hence in the cut height, was found to be too slow to carry out cuts with a vertical component, i.e. with a modifiable focal depth during cutting, with a speed that is comparable to the cut speeds in the horizontal work area.

US 2016/0089270 describes a system and a method for cutting lenticules in the eye tissue. According to US 2016/0089270, straight-lined fast scan lines are overlaid to this end on slower work lines that are traced out along meridians of the lenticule. Cuts that deviate in terms of their form from the desired surface curvature of the lenticule and consequently cause errors arise on account of the straight-line property of the fast scan lines. Moreover, a vertical focal displacement of the order and to the extent of the thickness of the lenticule to be cut is required in order to trace out the work lines along the meridians, in each case over the distance of a lenticule width; firstly, this is connected to corresponding outlay and costs for displaceable optical units and movable lenses that are configured to this end and, secondly, this is connected to losses in the work speed accompanying this. Moreover, on account of their fixed horizontal alignment, the fast scan lines do not allow best possible matching of cuts to lenticule surfaces, particularly not if these deviate from the spherical form.

SUMMARY

It is an advantage of the present disclosure to propose an apparatus for working on eye tissue by means of a pulsed laser beam, which does not have at least some of the disadvantages of the prior art.

According to the present disclosure, these advantages are achieved by the features of the independent claims. Moreover, further advantages emerge from the dependent claims and the description.

In one example, an ophthalmological apparatus for working on eye tissue, in particular for cutting a lenticule in the eye tissue, comprises a laser source that is configured to produce a pulsed laser beam; a focusing optical unit that is configured to focus the pulsed laser beam into the eye tissue; a scanner system, comprising a first scanner module and a second scanner module, for deflecting the pulsed laser beam onto work target points in the eye tissue; and a circuit for controlling the ophthalmological apparatus; and the aforementioned advantages are at least partially achieved by virtue of the circuit being configured to control the second scanner module in such a way that the second scanner module guides the pulsed laser beam in a feed direction onto work target points along a work line that extends along an outer face of a lenticule to be cut in the eye tissue, transversely to the meridians of the lenticule. The first scanner module is configured to guide the pulsed laser beam onto work target points along a scan line that extends across the work line at an alignment angle in a horizontal work plane, with a substantially higher scanning speed in comparison with the scanning speed of the second scanner module in the feed direction. The ophthalmological apparatus comprises a z-modulator that is configured to tilt the scan line out of the work plane depending on a specific work target point of the second scanner module on the work line such that the scan line runs substantially along the outer face of the lenticule. As a result of this tilt of the scanning line (that is scanned comparatively faster) depending on the current work target point of the work line (that is scanned comparatively slower), it is possible, in the eye tissue, to cut lenticules with a plurality of cut trajectories lying next to one another that are tilted out of the horizontal work plane without substantial deviations from the surface curvature of the lenticule to be cut being produced in the process. Particularly in comparison with solutions that have fixed horizontally aligned scan lines that do not permit ideal cut matching to the surface curvatures of lenticules, the dynamic change of the scan line tilt facilitates more flexible and precise cut matching to lenticule surfaces with a locally varying surface curvature. Depending on the selected form of the work line, it is moreover possible to cut the lenticules in the eye tissue without this requiring focal displacements, vertical thereto, of the order and to the extent of the entire depth of the vertical cut component to be performed, i.e. the thickness of the lenticule to be cut, by way of displacements of the projection optical unit or movements of lenses of a zoom system with a speed with which the second scanner module traces over a distance of the work line that corresponds to the lateral extent of the lenticule to be cut.

In one illustrative example variant, the ophthalmological apparatus comprises a rotator that is configured to rotate a fast scan plane defined by the scan line and the pulsed laser beam about an optical transmission axis in such a way that the alignment angle of the scan line is modified in relation to the work line.

In a further illustrative example variant, the circuit is configured to control the rotator depending on the specific work target point of the second scanner module on the work line such that the alignment angle of the scan line relative to the work line is set depending on the specific work target point of the second scanner module on the work line.

In one illustrative example variant, the ophthalmological apparatus comprises a scan length modulator that is configured to modify a length of the scan line. The circuit is configured to control the scan length modulator depending on the specific work target point of the second scanner module on the work line such that the length of the scan line is set depending on the specific work target point of the second scanner module on the work line.

In a further illustrative example variant, the circuit is configured to control the second scanner module in such a way that the second scanner module guides the pulsed laser beam onto work target points in the work plane along a circular or elliptical work line that extends along the outer face of the lenticule.

In one illustrative example variant, the circuit is configured to control the second scanner module in such a way that the second scanner module guides the pulsed laser beam in succession along a plurality of circular or elliptical work lines that are arranged in work planes lying above one another and that extend along the outer face of the lenticule.

In a further illustrative example variant, the circuit is configured to control the second scanner module in such a way that the second scanner module guides the pulsed laser beam onto work target points along a spiral work line that extends along the outer face of the lenticule.

In one illustrative example variant, the circuit is configured to control the second scanner module in such a way that the second scanner module guides the pulsed laser beam onto work target points along a work line that extends along the outer face of the lenticule in the form of a circular arc segment, a spiral arc segment or a curved line segment.

In a further illustrative example variant, the circuit is configured to control the second scanner module in such a way that the second scanner module guides the pulsed laser beam onto work target points along a plurality of spiral work lines, said work lines extending in a spiral arm shape in the direction of a centre of the outer face proceeding from a periphery of the outer face of the lenticule in a first step, and extending in a spiral arm shape to the periphery of the outer face of the lenticule proceeding from the centre in a second step.

In one illustrative example variant, the circuit is configured to control the second scanner module in such a way that the second scanner module guides the pulsed laser beam onto work target points along a plurality of spiral work lines, said work lines extending in a spiral arm shape in the direction of a centre of the outer face proceeding from a periphery of the outer face of the lenticule and ending at a specific distance from the centre in a first step, and extending in a spiral arm shape to the periphery of the outer face of the lenticule proceeding from the specific distance from the centre in a second step, or conversely, extending in a spiral arm shape to the periphery of the outer face of the lenticule proceeding from the specific distance from the centre in a first step and extending in a spiral arm shape in the direction of the centre of the outer face from the periphery of the outer face of the lenticule.

In a further illustrative example variant, the z-modulator is configured to bend the scan line in relation to the work plane. The circuit is configured to control the z-modulator depending on the specific work target point of the second scanner module on the work line in such a way that the z-modulator bends the scan line depending on the specific work target point of the second scanner module on the work line for the purposes of adaptation to the outer face of the lenticule.

In one illustrative example variant, the ophthalmological apparatus comprises a rotator that is configured to rotate a fast scan plane defined by the scan line and the pulsed laser beam about an optical transmission axis in order to modify the alignment angle of the scan line in relation to the work line. The z-modulator is configured to bend the scan line in relation to the work plane. The ophthalmological apparatus comprises a scan length modulator that is configured to modify a length of the scan line. The circuit is configured, depending on the specific work target point of the second scanner module on the work line, to control the rotator to set the alignment angle of the scan line in relation to the work line, to control the z-modulator to bend the scan line in relation to the work plane and to control the scan length modulator to set the length of the scan line in such a way that the outer face of the lenticule is cut in a predetermined free-form for the purposes of correcting a higher-order aberration.

In a further illustrative example variant, the ophthalmological apparatus comprises a rotator that is configured to rotate a fast scan plane defined by the scan line and the pulsed laser beam about an optical transmission axis in order to modify the alignment angle of the scan line in relation to the work line. The ophthalmological apparatus comprises a scan length modulator that is configured to modify a length of the scan line. The circuit is configured, depending on the specific work target point of the second scanner module on the work line, to control the rotator to set the alignment angle of the scan line in relation to the work line, to control the z-modulator to tilt the scan line in relation to the work plane and to control the scan length modulator to set the length of the scan line in such a way that the outer face of the lenticule is cut in a predetermined free-form for the purposes of correcting a higher-order aberration.

In one example, the ophthalmological apparatus for working on eye tissue comprises a laser source that is configured to produce a pulsed laser beam; a focusing optical unit that is configured to focus the pulsed laser beam into the eye tissue; and a scanner system that is configured to guide the pulsed laser beam onto work target points in the eye tissue; and the aforementioned advantages are at least partly achieved by virtue of the circuit being configured to control the scanner system in such a way that the scanner system guides the pulsed laser beam onto work target points in an area to be cut in a cornea, in work trajectories that extend next to one another, in order, initially, to produce cut trajectories, separated by remaining tissue bridges, of a tissue cut to be undertaken in the area and in order, thereafter, to guide the pulsed laser beam onto work target points in the remaining tissue bridges between the cut trajectories in the area in order to complete the tissue cut. Cutting cut trajectories that are separated by tissue bridges in each case facilitates the cut of a new cut trajectory without the latter being impaired by deformations that are caused by the formation of gas in an already cut, directly adjacent cut trajectory.

In one illustrative example variant, the ophthalmological apparatus comprises a measurement system that is configured to optically capture structures in the eye tissue. The circuit is configured to control the measurement system in such a way that the measurement system captures the produced cut trajectories and positions the work target points in the remaining tissue bridges on the basis of the captured cut trajectories. In one illustrative example variant, the measurement system is embodied as an interferometric measurement system. Capturing cut trajectories already cut and working on remaining tissue bridges taking account of the cut trajectories already cut facilitates a flexible adaptation to the actual form of performed cut trajectories and thereby facilitates an avoidance of, or at least reduction in, overlapping cut trajectories over extended regions.

In a further illustrative example variant, the circuit is configured to control the scanner system in such a way that the scanner system guides the pulsed laser beam with overlapping laser pulse spots onto successive work target points.

In one illustrative example variant, the circuit is configured to control the scanner system in such a way that the scanner system guides the pulsed laser beam onto work target points in the work trajectories extending next to one another into the remaining tissue bridges.

In a further illustrative example variant, the circuit is configured to control the scanner system in such a way that the scanner system guides the pulsed laser beam in the remaining tissue bridges onto work target points in work trajectories which have a width going beyond the tissue bridges.

In one illustrative example variant, the circuit is configured to control the scanner system in such a way that the scanner system guides the pulsed laser beam onto work target points in work trajectories that extend parallel next to one another.

In a further illustrative example variant, the circuit is configured to control the scanner system in such a way that the scanner system guides the pulsed laser beam onto work target points in work trajectories that extend next to one another, said work trajectories having a spiral, circular or elliptical form.

In one illustrative example variant, the circuit is configured to control the scanner system in such a way that the scanner system guides the pulsed laser beam in a feed direction onto work target points along a work line extending in the work trajectories. The scanner system is configured to guide the pulsed laser beam along a scan line, extending across the work line, within the work trajectories with a substantially higher scan speed in comparison with the scan speed in the feed direction.

In a further illustrative example variant, the circuit is configured to control the scanner system in such a way that the scanner system guides the pulsed laser beam onto work target points on an outer side of a lenticule to be cut in a cornea, in the work trajectories extending next to one another, in order to produce the cut trajectories of the tissue cut to be undertaken at the outer face of the lenticule, said cut trajectories being separated by remaining tissue bridges, and thereafter guides the pulsed laser beam onto work target points in the remaining tissue bridges between the cut trajectories on the outer face of the lenticule in order to complete the tissue cut.

In one illustrative example variant, the circuit is configured to control the scanner system in such a way that the scanner system guides the pulsed laser beam onto work target points onto the lower outer face of the lenticule to be cut, facing away from an outer corneal surface, in order to produce the cut trajectories, separated by remaining tissue bridges, on the lower outer face of the lenticule to be cut and that the scanner system thereupon guides the pulsed laser beam onto work target points on an upper outer face of the lenticule be cut, facing the outer corneal surface, in work trajectories extending next to one another, in order to produce cut trajectories, separated by remaining tissue bridges, of an upper tissue cut to be undertaken on the upper outer face of the lenticule before the scanner system guides the pulsed laser beam onto the work target points into the remaining tissue bridges on the lower outer face of the lenticule in order to complete the lower tissue cut; and that the scanner system thereupon guides the pulsed laser beam onto work target points into the remaining tissue bridges on the upper outer face of the lenticule in order to complete the upper tissue cut.

In a further illustrative example variant, the ophthalmological apparatus comprises a measurement system that is configured to optically capture structures in the eye tissue. The circuit is configured to control the measurement system in such a way that the measurement system captures the produced cut trajectories of the lower tissue cut to be undertaken and positions, in respect of the captured cut trajectories of the lower tissue cut, the work trajectories of the upper tissue cut to be undertaken. In one illustrative example variant, the measurement system is embodied as an interferometric measurement system.

In a further illustrative example variant, the circuit is configured to determine the work trajectories of the upper tissue cut to be undertaken with a smaller trajectory width in respect of the captured cut trajectories of the lower tissue cut.

In one illustrative example variant, the circuit is configured to position the work trajectories for completing the lower tissue cut in relation to the captured cut trajectories of the lower tissue cut.

In one example, the ophthalmological apparatus for working on eye tissue comprises a laser source that is configured to produce a pulsed laser beam; a focusing optical unit that is configured to focus the pulsed laser beam into the eye tissue; and a scanner system that is configured to guide the pulsed laser beam onto work target points in the eye tissue; a measurement system that is configured to optically capture structures in the eye tissue; and a circuit that is configured to control the scanner system in such a way that the scanner system guides the pulsed laser beam onto work target points on a first outer face of a lenticule to be cut in the eye tissue in order to produce a first tissue cut for cutting the lenticule;

and the aforementioned advantages are at least partly achieved by virtue of the circuit moreover being configured to control the measurement system in such a way that the measurement system captures the first outer face of the lenticule that is produced by the first tissue cut and to control the scanner system in such a way that the scanner system guides the pulsed laser beam onto work target points on a second outer face, positioned in relation to the captured first outer face of the lenticule, of the lenticule to be cut in order to produce a second tissue cut, positioned in relation to the captured first outer face of the lenticule, for cutting the lenticule. In one illustrative example variant, the measurement system is embodied as an interferometric measurement system. Capturing a tissue cut on a first outer face of a lenticule to be cut and, dependent thereon, positioning and carrying out a tissue cut on a second outer face of the lenticule facilitates a flexible and precise adaptation of form and orientation of the tissue cut to be carried out or of the second outer face in relation to the actual orientation and form of the tissue cut already carried out and thereby brings about an improvement in form and size of the lenticule, in particular in the thickness thereof, and in the desired refractive correction of the eye achievable therewith. In one illustrative example variant, the circuit is configured to position the second outer face of the lenticule to be cut, with a predetermined centre thickness of the lenticule to be cut, in relation to the captured first outer face.

In a further illustrative example variant, the circuit is configured to position the second outer face of the lenticule to be cut, with a predetermined thickness profile of the lenticule to be cut, in relation to the captured first outer face.

In one illustrative example variant, the circuit is configured to control the measurement system in such a way that the measurement system captures deformations of the first outer face caused by gas bubbles produced during the first tissue cut and positions the second outer face of the lenticule to be cut taking account of the captured deformations in respect of the captured first outer face.

In a further illustrative example variant, the circuit is configured to determine the first outer face of the lenticule to be cut as a lower side of the lenticule to be cut facing away from an outer corneal surface and to determine the second outer face of the lenticule to be cut as an upper side of the lenticule to be cut facing the outer corneal surface.

In an illustrative example variant, the circuit is configured to control the scanner system in such a way that the scanner system guides the pulsed laser beam onto work target points in work trajectories extending next to one another on the first outer face of the lenticule to be cut in order to produce cut trajectories of the first tissue cut extending next to one another; and to control the measurement system in such a way that the measurement system captures the cut trajectories extending next to one another and positions the second outer face of the lenticule to be cut in relation to the captured cut trajectories extending next to one another.

In a further illustrative example variant, the circuit is configured to control the scanner system in such a way that the scanner system guides the pulsed laser beam onto work target points in work trajectories extending next to one another on the first outer face of the lenticule to be cut in order to produce cut trajectories of the first tissue cut that extend next to one another and that are separated by remaining tissue bridges; to control the measurement system in such a way that the measurement system captures the cut trajectories; and to control the scanner system in such a way that the scanner system guides the pulsed laser beam onto work target points in the remaining tissue bridges, determined on the basis of the captured cut trajectories, on the first outer face in order to produce the first tissue cut.

In one illustrative example variant, the circuit is configured to control the scanner system in such a way that the scanner system guides the pulsed laser beam onto work target points in work trajectories that extend on the outer face of the lenticule and that have a configuration that is straight lined, that extends along circles, that is concentrically circular, that is concentrically elliptical, that is spiral-shaped or that is spiral-arm-shaped.

In a further illustrative example variant, the circuit is configured to control a second scanner module of the scanner system in such a way that the second scanner module guides the pulsed laser beam onto work target points in a feed direction along a work line that extends on the first and/or second outer face of the lenticule to be cut; that the scanner system comprises a first scanner module that is configured to guide the pulsed laser beam along a scan line extending across the work line at an alignment angle in the horizontal work plane, with a substantially higher scan speed in comparison with the scan speed of the second scanner module in the feed direction; and that the scanner system comprises a z-modulator that is configured to tilt the scan line out of the work plane depending on a specific work target point of the second scanner module on the work line in such a way that the scan line extends substantially along the outer face of the lenticule.

BRIEF DESCRIPTION OF THE DRAWINGS

An illustrative example of the present disclosure is described below on the basis of an example. The example of the illustrative example is illustrated by the figures attached below.

DETAILED DESCRIPTION

Figure 1:
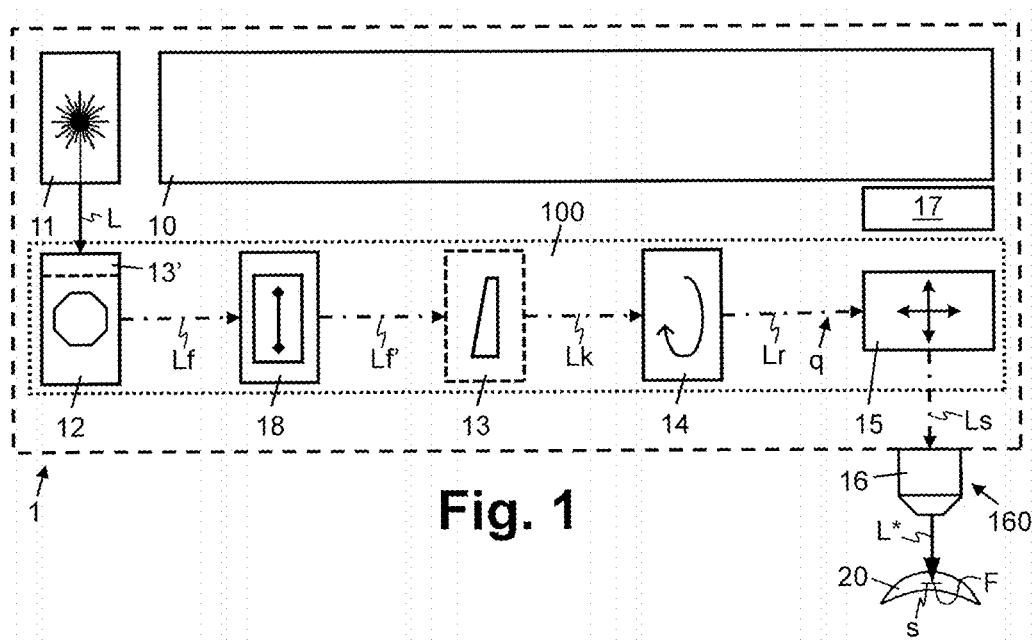
FIG. 1 shows a block diagram that schematically illustrates an ophthalmological apparatus for working on eye tissue with a pulsed laser beam, said apparatus comprising a scanner system for scanning the eye tissue with the pulsed laser beam at work target points in the eye tissue.
Figure 2A:
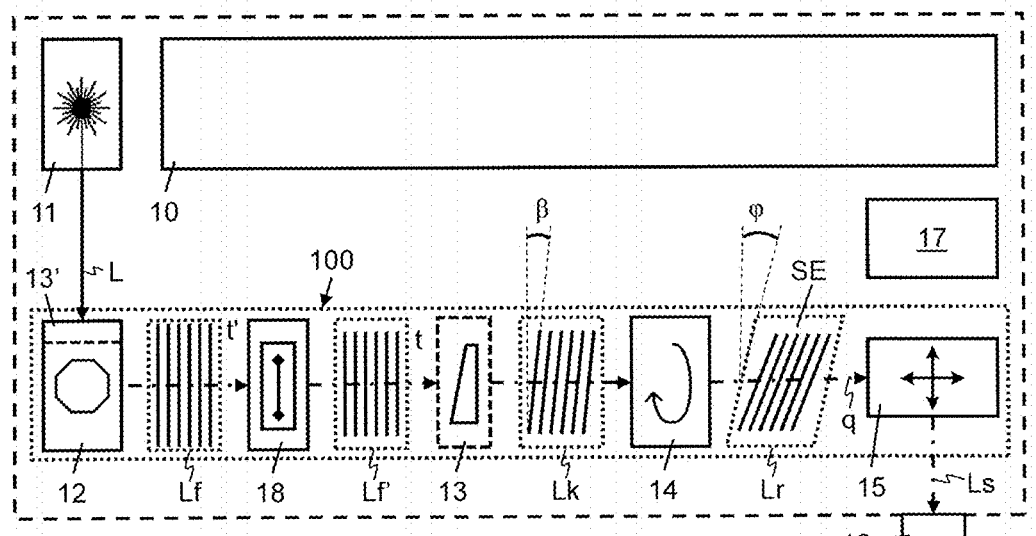
FIG. 2a shows a schematic plan view of an eye tissue region, which illustrates a work line in the feed direction and a scan line extending across the work line.
Figure 2A:
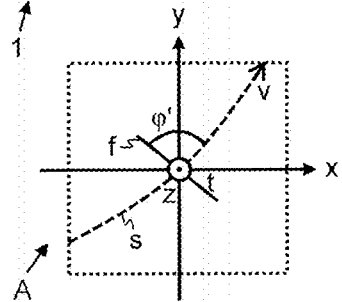
Figure 2B:
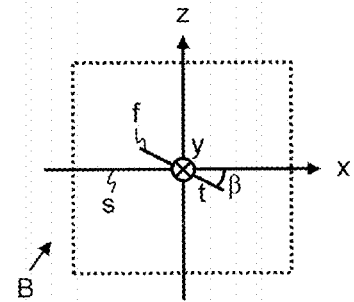
FIG. 2b shows a schematic cross-sectional view of an eye tissue region, which illustrates a work line that extends in a work plane extending perpendicular to the plane of the drawing, and a scan line that is tilted out of the work plane.
Figure 2:
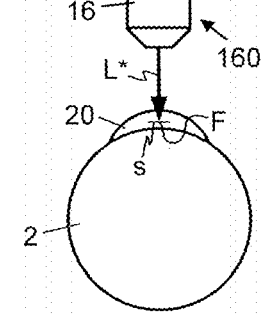
FIG. 2 shows a block diagram of the ophthalmological apparatus, which illustrates a plurality of modules of the scanner system that contribute to guiding the pulsed laser beam along a scan line extending across a work line.

In FIGS. 1 and 2, the reference sign 1 in each case relates to an ophthalmological apparatus for working on eye tissue 20, for example the cornea or any other tissue of an eye 2, by means of laser pulses.

As illustrated schematically in FIGS. 1 and 2, the ophthalmological apparatus 1 comprises a scanner system 100 for guiding a pulsed laser beam L, supplied by a laser source 11, via a focusing optical unit 16 onto work target points F in the eye tissue 20, and a measurement system 17 for optically capturing structures in the eye tissue 20. The measurement system 17 is embodied as an imaging measurement system, in particular as an interferometric measurement system.

The focusing optical unit 16 is configured for focused projection of the pulsed laser beam L and/or the laser pulses for point-by-point disintegration of tissue in a focus F at a work target point in the interior of the eye tissue 20. In FIGS. 1 and 2, the laser beam L that has been focused by the focusing optical unit 16 is denoted by the reference sign L*.

By way of example, the focusing optical unit 16 is installed in an application head 160, which can be placed onto the eye 2. The application head 160 is preferably placed onto the eye 2 by way of an at least partly light-transparent contact body or a fluid chamber and it is fastened to the eye 2 by means of a vacuum-controlled suction ring, for example, with the contact body and the suction ring being connected to the application head 160 in a fixed or removable manner. In one illustrative example variant, the focusing optical unit 16 comprises a focus adjustment device for setting the focal depth, for example one or more movable lenses, in the focusing optical unit 16 or upstream of the focusing optical unit 16, or a drive for moving the entire focusing optical unit 16.

In particular, the laser source 11 comprises a femtosecond laser for producing femtosecond laser pulses, which have pulse widths of typically 10 fs to 1000 fs (1 fs=$10^{-15}$ s). The laser source 11 is arranged in a separate housing or in a housing shared with the focusing optical unit 16.

It should be noted here that the reference sign L denotes, in general, the pulsed laser beam L and/or the laser pulses thereof in the beam path from the laser source 11 to the focus F, but that, depending on the context, further reference signs are also used to denote the pulsed laser beam L and/or the laser pulses thereof at a specific point in the beam path and/or in the scanner system 100.

It is clear from FIGS. 1 and 2 that the scanner system 100 comprises a plurality of optical functional modules, a first scanner module 12 (fast-scan module), a scan length modulator 18, a z-modulator 13 and/or 13', a rotator 14 and a second scanner module 15 (slow-scan module). A person skilled in the art will understand that it is possible to dispense with the scan length modulator 18, the z-modulator 13, 13' and/or the rotator 14 depending on the functions to be carried out by the ophthalmological apparatus 1, which functions will be described herein below. The first scanner module 12 in the ophthalmological apparatus 1 is also optional.

As illustrated schematically in FIGS. 1 and 2, the ophthalmological apparatus 1 comprises a circuit 10 for controlling the laser source 11, the optical functional modules of the scanner system 100, the focusing optical unit 16 and the measurement system 17. The circuit 10 realizes a programmable control apparatus and comprises e.g. one or more processors with program and data memory and programmed software modules for controlling the processors, and/or other programmable circuits or logic units such as ASICs (application specific integrated circuits).

The scanner module 15 (slow-scan module) disposed upstream of the focusing optical unit 16 is configured to scan the eye tissue with the pulsed laser beam L and/or the laser pulses in an x/y-work plane along a work line s, as illustrated in an exemplary manner in the plan view A of FIG. 2a. The scanner module 15 is embodied as a mechanical scanner that drives the focusing optical unit 16 over a work area along the work line s by means of one or more movement drivers such that the focus F is guided along the work line s in the x/y-work plane, or the scanner module 15 has a beam-deflecting illustrative example and comprises one or two deflection mirrors, each movable about one or two axes, for deflecting the pulsed laser beam L and/or the laser pulses in the x/y-work plane along the work line s. The beam-deflecting scanner module 15 is embodied as a freely addressable scanner and comprises e.g. a galvano scanner or a piezo-driven scanner.

The scanner module 12 (fast-scan module) disposed upstream of the scanner module 15 is configured to scan the eye tissue with the pulsed laser beam L and/or the laser pulses along a scan line f that is overlaid on the work line s, as illustrated in an exemplary manner in the plan view A of FIG. 2a. The two scanner systems 12 and 15 are configured and coupled in such a way that the scan movement extending along the scan line f is overlaid on the work line s of the scanner module 15. The scan line f extends across the work line s at an alignment angle φ'. The alignment angle φ' between the scan line f and the work line s is adjustable by way of the rotator 14. The scanner module 12 comprises one or more movable deflection mirrors, for example a rotating polygon mirror (polygon scanner), one or more resonant mirrors (resonant scanner) or oscillating mirrors (oscillating scanner), which are e.g. piezo-driven (piezo-scanner), or MEM (micro-electromechanical) scanners, or the scanner module 12 comprises an AOM (acousto-optic modulator) scanner or an EOM (electro-optic modulator) scanner. The scanner module 12 has a higher, e.g. multiply higher, scan speed than the downstream scanner module 15. Accordingly, the scanner module 12 can also be referred to as fast-scan module, which produces the deflected laser beam Lf, and the scanner module 15 can be referred to as slow-scan module, which produces the deflected laser beam Ls.

Figure 16:
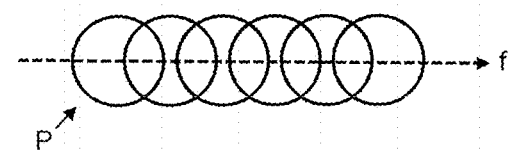
FIG. 16 shows a schematic plan view of overlapping laser pulse spots of a pulsed laser beam along a scan line.

As illustrated in FIG. 16, in one variant, the pulsed laser beam is guided by the scanner system 100 and/or by the scanner module 12 onto work target points F along the scan line f in such a way that the laser pulse spots P of the pulsed laser beam partly overlap along the scan line f, as a result of which tissue bridges along the scan line f are prevented. The degree of overlap is adjustable depending on the scanning speed of the scanner module 12 and the pulse rate of the laser source 11.

As illustrated schematically in FIGS. 1 and 2, the scan length modulator 18 is disposed downstream of the scanner module 12 and configured to modify the length t of the scan line f. In one illustrative example variant, the scan length modulator 18 comprises an adjustable stop to this end, said stop being coupled to an actuatable drive (electric motor). As illustrated schematically in FIG. 2, the scan length modulator 18 reduces the length t' of the scan line f in the deflected laser beam Lf produced by the scanner module 12 to the intended length t of the scan line f in the laser beam Lf' that is deflected by the scanner module 12 and delimited by the scan length modulator 18.

As illustrated schematically in FIGS. 1 and 2, the z-modulator denoted by reference sign 13 is disposed downstream of the scanner module 12 or, in an alternative illustrative example denoted by reference sign 13', it is disposed upstream of the scanner module 12. The z-modulator 13 and/or 13' is configured to tilt the scan line f out of the x/y-work plane of the scanner module 15, for example by the tilt angle β, as illustrated schematically in the cross-sectional view B of FIG. 2b, and/or to bend the scan line f with a dynamically modifiable tilt angle β in respect of the x/y-work plane of the scanner module 15. As illustrated schematically in FIG. 2, the z-modulator 13, 13' produces a divergence-modulated laser beam Lk with the resultant tilt and/or curvature of the scan line f.

In the variant disposed downstream of the scanner module 12, the z-modulator 13 comprises one or more optical elements disposed upstream of the focusing optical unit 16, said optical elements being arranged in the beam path from the scanner module 12 to the focusing optical unit 16 and being configured to produce, in the beam path, a divergence of the laser beam L that depends on the scan angle of the scanner module 12. Illustrative examples of the optical elements of the z-modulator 13 comprise wedge plates, prisms, lenses, diffractive optical elements and aspherical mirrors, for example. The optical elements of the z-modulator 13 are securely installed or, in one variant for setting the divergence of the laser beam L that depends on the scan angle of the scanner module 12, can be pushed into the beam path and/or pushed out of the beam path. As an alternative, or additionally, the optical elements of the z-modulator 13 can be set or are adjustable for setting the divergence of the laser beam L that depends on the scan angle of the scanner module 12, for example by rotating the optical elements about the optical axis q, by tilting the optical elements about an axis of rotation or by displacing the optical elements along a translation axis that is tilted in relation to the optical axis q. In an alternative illustrative example variant, the optical element 13 is arranged directly in the scanner module 12 and embodied, for example, as a deflection mirror that has a changeable surface curvature.

Figure 3:
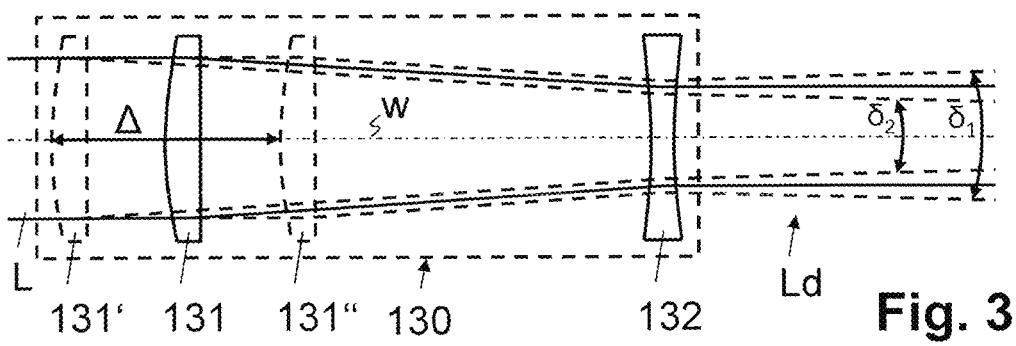
FIG. 3 shows a schematic cross section of a portion of the beam path in a divergence modulator with at least one displaceable lens and illustrates the divergence of the laser beam that is modified by displacing the lens.

In the variant disposed upstream of the scanner module 12, the z-modulator 13' is embodied as a divergence modulator 130 that is configured to dynamically change the divergence of the laser beam L. FIG. 3 schematically illustrates an illustrative example variant of the z-modulator 13' or the divergence modulator 130 with two optical lenses 131, 132 arranged in series, at least one of said lenses being displaceable on an optical transmission axis w for modulating the divergence of the laser beam L. For the purposes of the dynamic modulation of the divergence of the laser beam L, the movable lens 131 is coupled to a movement driver. As is visible in the example of FIG. 3, the laser beam L in a first basic position 131' of the movable lens has a corresponding divergence $\delta_1$. When displacing the movable lens 131 along the transmission axis w, there is a continuous change in the divergence of the laser beam L and it has a modified divergence $\delta_2$ at the position 131" that is displaced by the deflection distance Δ.

In alternative illustrative example, the z-modulator 13' comprises a spatial light modulator for modulating the wavefront of the laser beam L, a spatial light modulator for modulating the reflection angle at a plurality of points of a reflection face over which the laser beam L is guided, a refractive index modulator for modulating the refractive index of an optical element at a plurality of points in the cross section of the beam path and/or an amplitude modulator for modulating the amplitude at a plurality of points in the cross section of the beam path, i.e. in the beam profile, of the laser beam L.

In a further variant, the z-modulator is configured to (adjustably) tilt the focusing optical unit 16 about an axis of rotation that extends perpendicular to a plane defined by the work line s and the optical axis of the focusing optical unit 16 in order thereby to tilt the scan line f out of the x/y-work plane of the scanner module 15 by an adjustable tilt angle.

As a result of the divergence modulation, there is a displacement of the focus F of the laser beam L depending on the scan angle of the scanner module 12 in the projection direction and this produces a tilted or curved scan line f. The z-modulator 13, 13' or divergence modulator 130 is coupled to the scanner module 12 in such a way that the change in the divergence $\delta_1$, $\delta_2$ of the laser beam L can be synchronized with the scan angle of the scan movement such that this yields a divergence $\delta_1$, $\delta_2$ of the laser beam L that changes with the scan angle of the scanner module 12, i.e., that is dependent on the scan angle. The z-modulator 13, 13' and/or divergence modulator 130 is configured to modulate the divergence $\delta_1$, $\delta_2$ of the laser beam L during the scan movement with a frequency or speed that is at least as large as that with which the scanner module 12 carries out the scan movement over the scan angle in order to bring about a tilt of the scan line f. In order to bring about a "non-linear tilt" and hence a deformation (bend) of the scan line f in the projection direction, the z-modulator 13, 13' or divergence modulator 130 is configured to modulate the divergence $\delta_1$, $\delta_2$ of the laser beam L during the scan movement with frequency components or speed that is greater than that with which the scanner module 12 carries out the scan movement over the scan angle.

As illustrated in FIGS. 1 and 2, the rotator 14 is disposed downstream of the scanner module 12 in the beam path and configured to rotate the fast-scan plane Lf, which is defined by the scan movement of the scanner module 12 and the optical transmission axis q, about an angle of rotation ϕ about the optical transmission axis q such that a fast-scan plane SE that is rotated through the angle of rotation ϕ is defined, as illustrated schematically in FIG. 2. In FIG. 2, the laser beam L with the fast-scan plane rotated by the rotator 14 is denoted by the reference sign Lr. In one illustrative example variant, the rotator 14 comprises a K-mirror or a prism for rotating the fast-scan plane Lf.

For the better understanding of FIG. 2, it should be noted here that a multiplicity of (length-modulated, tilted and rotated) scan lines are reproduced in the schematic illustration of the rotated fast-scan plane SE, said scan lines being produced upstream by the scanner module 12 by deflecting the pulsed laser beam L, being restricted in terms of their length to the length t' by the scan length modulator 18, being tilted and/or bent by the z-modulator 13, 13' or divergence modulator 130, and finally being rotated by the rotator 14 about the optical transmission axis q.

By controlling the scanner module 12 (fast-scan module) and the scanner module 15 (slow-scan module), the pulsed laser beam is guided in the feed direction v along a work line s onto work target points F in the eye tissue 20 and the eye tissue 20 is scanned in working-on fashion along scan lines f, which, overlaid on the work line s, extend across the work line s. In combination with an appropriate control of the functional modules of the scanner system 100 by the circuit 10, the scan line f is dynamically set and modified in the process in terms of its length t, t' by the scan length modulator 18, in terms of its tilt and/or curvature in relation to the x/y-work plane by the z-modulator 13, 13' and in terms of its alignment in the x/y-work plane in relation to the work line s by the rotator 14 such that areas with any predetermined free-form are cut in the eye tissue 20. By cutting two such cut faces in the eye tissue 20, lenticules 21 of any predetermined free-form are cut in the eye tissue, as a result of which even the correction of higher order aberrations is facilitated.

In the following paragraphs, examples of possible cut methods and cut forms are described with reference to FIGS. 4-16, said cut methods and cut forms being carried out with an appropriately configured circuit 10 and the control of the ophthalmological apparatus 1 and/or the functional modules of the scanner system 100 carried out therewith.

Figure 4:
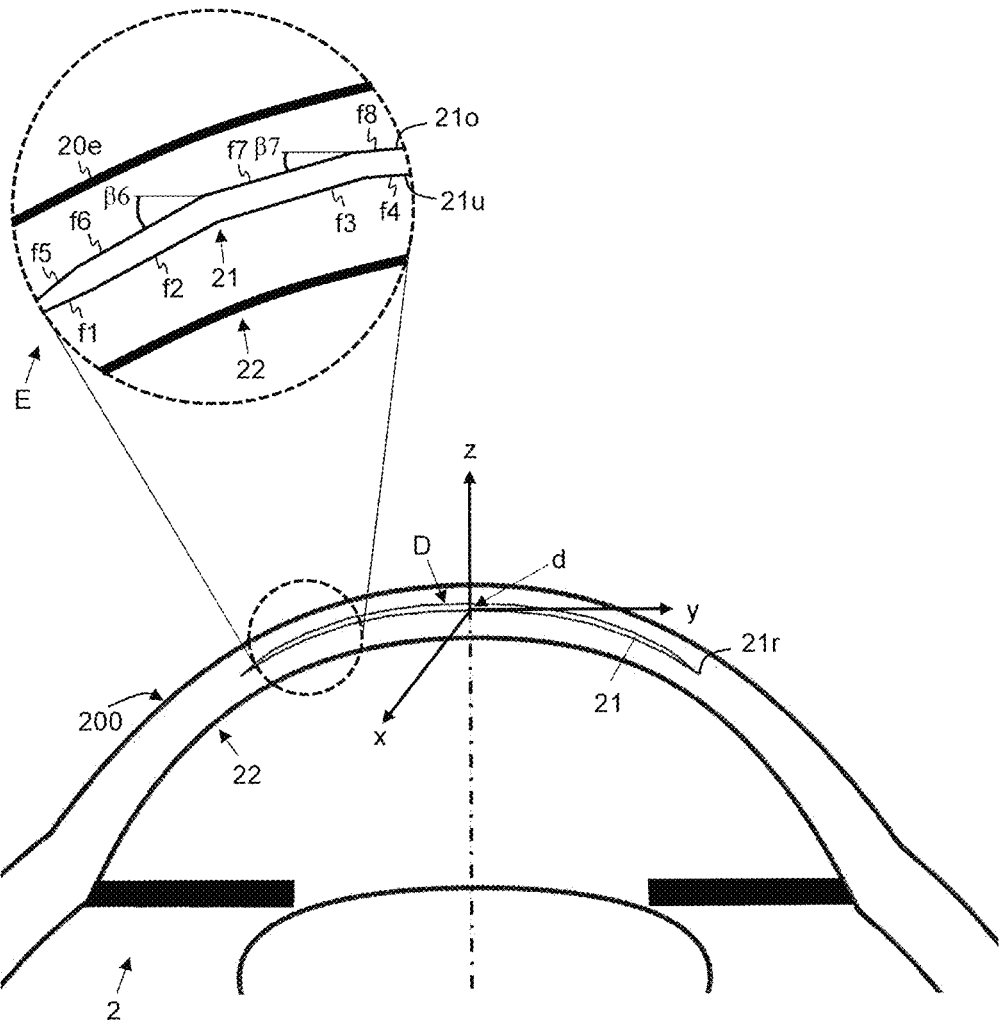
FIG. 4 shows a schematic cross-sectional view of an eye tissue region with a lenticule cut in the cornea and a portion thereof reproduced in a magnified manner.

In a cross-sectional view normal to the x/y-work plane, FIG. 4 illustrates cutting a lenticule 21 in the cornea 22 of an eye 2 by means of a multiplicity of adjoining cut trajectories that are produced by scanning the cornea 22 in working-on fashion using the pulsed laser beam L on work target points F along scan lines f1, f2, f3, f4, f5, f6, f7, f8, as is visible in the section E illustrated in magnified fashion. Here, the cut trajectories or the scan lines f1, f2, f3, f4, f5, f6, f7, f8 carried out to this end are tilted in each case by a different tilt angle β5, β6, β7, β8 in relation to the x/y-work plane by means of the z-modulator 13, 13', as explicitly specified in the section E, illustrated in magnified fashion, for the cut trajectories or scan lines f5, f6, f7, f8 of the upper outer face 21o of the lenticule and as likewise visible in the cut trajectories or scan lines f1, f2, f3, f4 of the lower outer face 21u of the lenticule 21. As a result of the individually set tilt angles β5, β6, β7, β8 of the scan lines f1, f2, f3, f4, f5, f6, f7, f8, the curve is adapted to the best possible extent to the form (gradient) of the outer faces 21o, 21u of the lenticule 21 to be cut. The upper and lower outer faces 21o, 21u meet at the peripheral edge 21r of the lenticule 21 to be cut, which is embodied as a cylindrical area in one variant.

In the plan view of the x/y-work plane, FIGS. 5, 6, 7, 8, 9 and 10 illustrate different work lines s for cutting the lenticule 21 in the cornea 22 of an eye 2 by means of scan lines f, which are overlaid on the respective work lines s and (as illustrated in FIG. 2a) have an orientation angle ϕ' in relation to the work line s. As is visible in FIGS. 5, 6, 7, 8, 9 and 10, the work lines s extend across the meridians m of the lenticule 21; i.e., the work lines s do not extend along the meridians m of the lenticule 21 but instead cut at least one of the meridians m of the lenticule 21. The work lines s according to FIGS. 5, 6, 9 and 10 each extend in the x/y-work plane, to be precise at different heights or depths in the z-direction, but there is no need for a change in the z-direction while scanning a closed work line s by the second scanner module 15. In the work lines s according to FIGS. 7, 8, 12 and 13, an adjustment in the z-direction is required while scanning a work line s by the second scanner module 15. Depending on the illustrative example of the second scanner module 15, the z-component of these height-varying work lines s are adapted to the outer faces 21o, 21u by an appropriate control of the second scanner module 15 or a separate focusing apparatus by way of the circuit 10. In a further illustrative example variant, an adjustable optical unit (e.g. with displaceable lenses) that is disposed upstream of the focusing optical unit 16 and disposed upstream or downstream of the z-modulator 13, 13' is provided to this end, said adjustable optical unit being configured to displace the scan line f that was tilted or bent by the z-modulator 13, 13' vertically in the z-direction. However for the purposes of improved understanding, it should be noted here that such adjustable optical units cannot fulfil the advantage of the z-modulator 13, 13' or divergence modulator 130 as, firstly, they are not synchronized with the scanner module 12 and, secondly, they also cannot carry out a focus displacement in the z-direction sufficiently quickly in order to be able to be synchronized with the scan movement or the corresponding scan angle of the scanner module 12 (fast-scan module). Also, these adjustable optical units do not facilitate an adjustable tilt of the scan line f, as is achieved by the variant in which the z-modulator tilts the focusing optical unit 16 about an axis of rotation.

Figure 5:
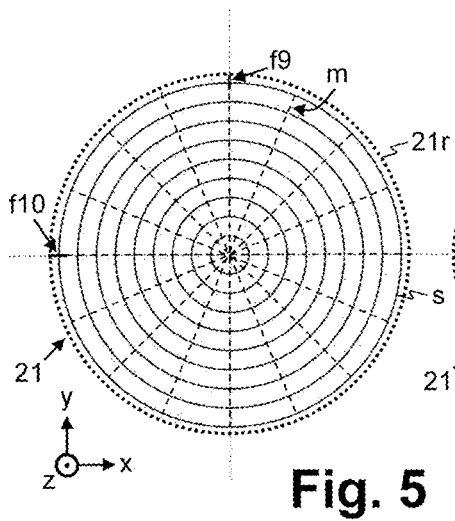
FIG. 5 shows a schematic plan view of a lenticule in the eye tissue, which is cut by a plurality of concentric circular work lines that extend across meridians of the lenticule and by scan lines extending thereacross.
Figure 6:
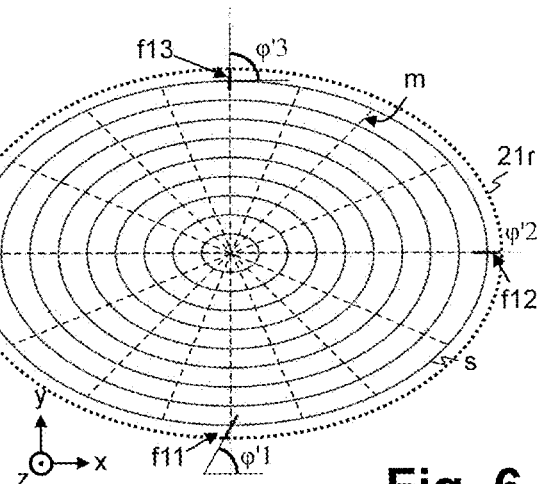
FIG. 6 shows a schematic plan view of a lenticule in the eye tissue, which is cut by a plurality of concentric elliptical work lines that extend across meridians of the lenticule and by scan lines extending thereacross.
Figure 7:
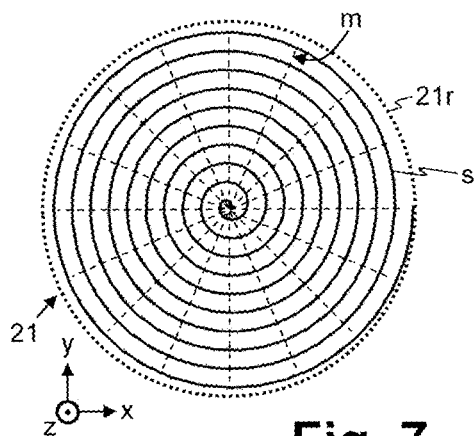
FIG. 7 shows a schematic plan view of a lenticule in the eye tissue, which is cut by a spiral work line that extends across meridians of the lenticule and by scan lines extending thereacross.
Figure 8:
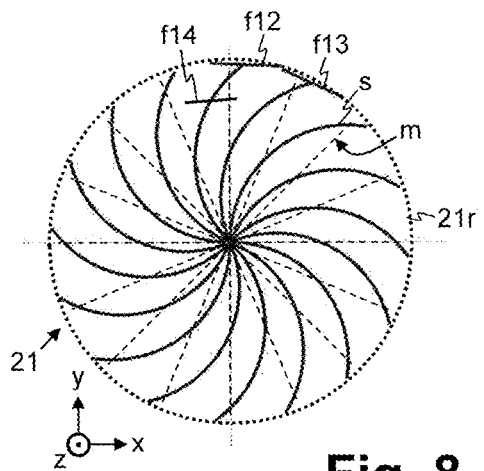
FIG. 8 shows a schematic plan view of a lenticule in the eye tissue, which is cut by spiral-arm-shaped work lines that extend across meridians of the lenticule and by scan lines extending thereacross.
Figure 9:
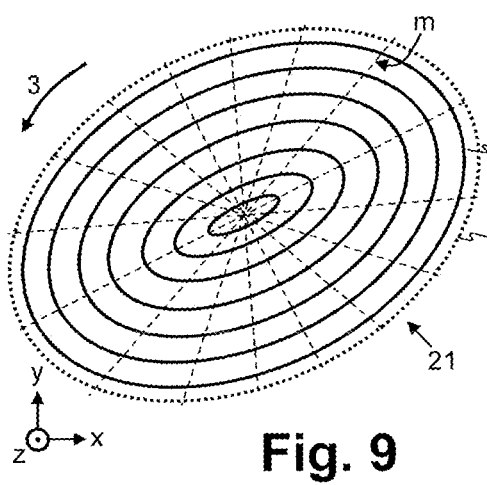
FIG. 9 shows a schematic plan view of a lenticule in the eye tissue, which is cut by a plurality of concentric work lines that extend across meridians of the lenticule and by scan lines extending thereacross.
Figure 10:
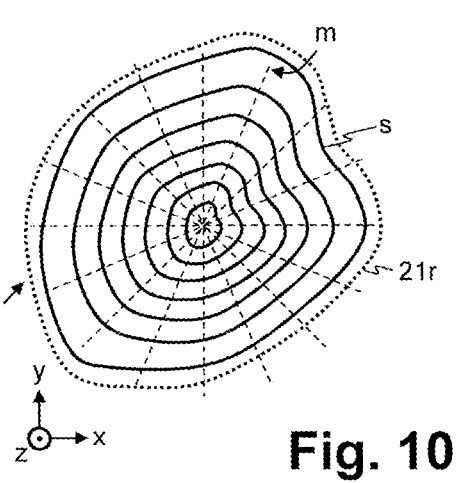
FIG. 10 shows a schematic plan view of a lenticule in the eye tissue, which is cut by a plurality of concentric curved work lines that extend across meridians of the lenticule and by scan lines extending thereacross.

FIG. 5 shows a cut implementation with a plurality of circular work lines s that are arranged concentrically to the optical axis of the eye 2. FIG. 6 shows a cut implementation with a plurality of elliptical work lines s that are arranged concentrically to the optical axis of the eye 2. FIG. 7 shows a cut implementation with a spiral work line s with a centre of the spiral on the optical axis of the eye 2. FIG. 8 shows a cut implementation with a plurality of spiral-arm-shaped work lines s that run towards a centre point on the optical axis of the eye 2 proceeding from the peripheral edge 21r of the lenticule 21 (or vice versa). FIG. 9 shows a cut implementation with a plurality of elliptical work lines s that are arranged concentrically to the optical axis of the eye 2, with the longitudinal and transverse axes of the lenticule 21s being rotated in the x/y-work plane about the optical axis of the eye 2, as indicated by the arrow 3, in contrast to the lenticule 21 of FIG. 6. FIG. 10 shows a cut implementation with a plurality of work lines s, which are each defined by a free-form closed curve.

Compared to the cut implementation according to FIGS. 5 and 6, the cut implementation according to FIG. 7 is advantageous in that it facilitates a slow and continuous height adjustment of the work line s, and hence of the scan line f extending thereacross, when cutting a (three-dimensional) lenticule 21; that is to say, it is possible to dispense with discontinuous and faster changes in the z-direction.

Figure 12:
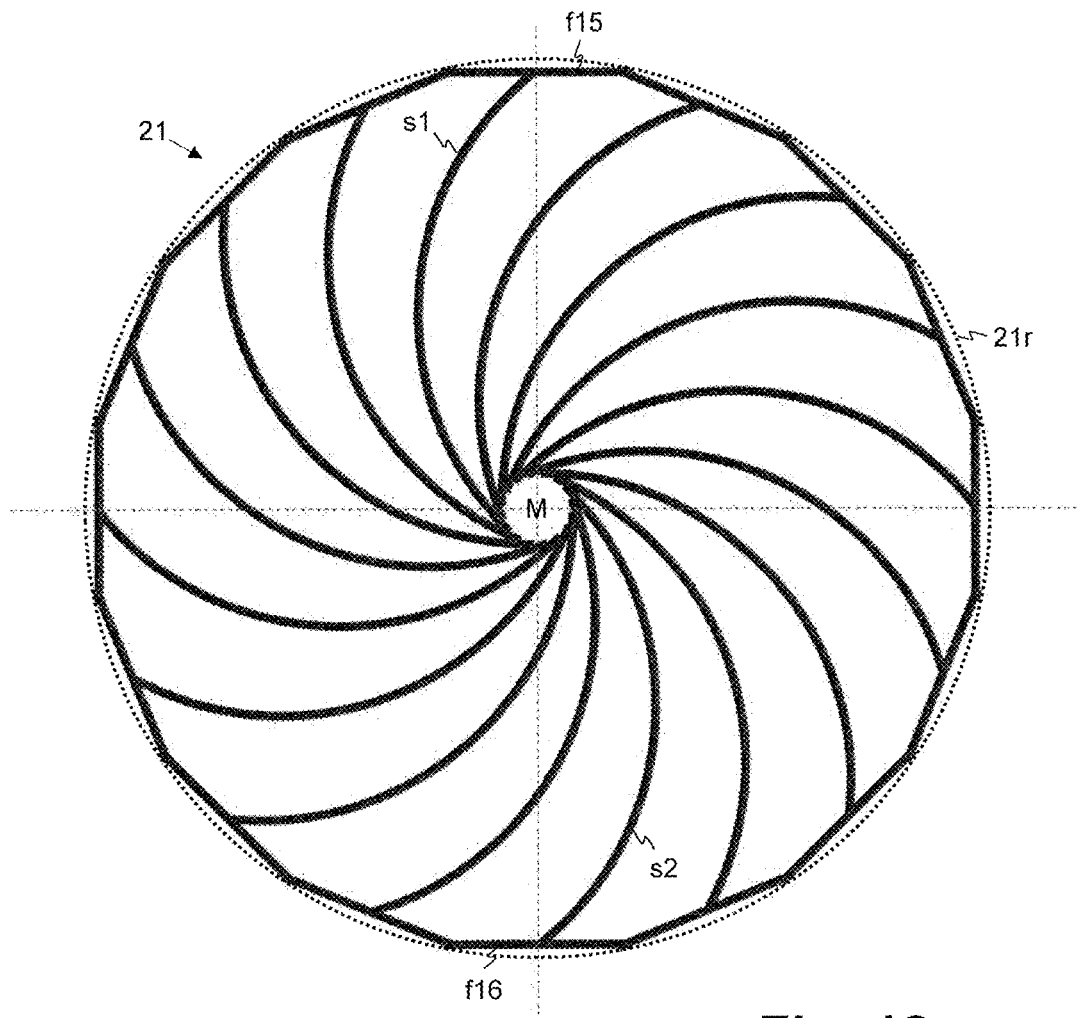
FIG. 12 shows a schematic plan view of a lenticule in the eye tissue, which is cut by spiral-arm-shaped, elliptical work lines that extend across meridians of the lenticule and by scan lines extending thereacross.

The advantage of the cut implementation according to FIGS. 8 and 12 consists of no periodic structures, which could lead to bothersome influences on the imaging when seeing, being produced in relation to the optical axis of the eye 2 since the rotation of the scan line f has a lower measure of preferred (accumulated) orientation (alignment).

As illustrated in FIGS. 5, 6, 7, 8, 9 and 10, the alignment or the alignment angle φ' of the scan line f in relation to the work line s by way of the rotator 14, controlled by the circuit 10, is dynamically modified and set during the work depending on the current position of the work target point F on the work line s. Thus, in the cut implementation of FIG. 5, the scan lines f9, f10 each have an alignment angle φ' of 90°, i.e. a normal alignment of the work line s, which is achieved by the rotator 14 by continuous adjustment and adaptation of the angle of rotation φ to the work line s.

In the cut implementation according to FIG. 6, the scan line f11 is aligned in relation to the work line s with an alignment angle φ'1 that is not rotated normally in relation to the work line s such that, in comparison with a scan line f that is aligned normally to the work line s, a narrower work trajectory or cut trajectory is produced in the narrower region of the elliptical lenticule 21 during the work. The scan line f12 is aligned normally to the work line s with the alignment angle φ'2 in order to produce a wider work trajectory or cut trajectory in the longer region of the elliptical lenticule 21. Finally, the scan line f13 is aligned normally to the work line s with the alignment angle φ'3; however, in comparison to the scan lines f11 and f12, it has a shorter length t, set by the scan length modulator 18, in order to produce a narrower work trajectory or cut trajectory in the narrower region of the elliptical lenticule 21 during the work.

In the cut implementations according to FIGS. 7 and 9, too, the scan lines overlaid on the spiral work line s or the elliptical work lines s are in each case dynamically modified and set in respect of their alignment angle φ' to the work line s, their length t and/or their tilt angle β or their curvature during the work depending on the current position of the work target point F on the work line s in order to produce the lenticule 21 with spiral or elliptical work trajectories or cut trajectories.

In the cut implementation according to FIG. 8, the alignment angle φ', the length t and the tilt angle β or the curvature of the scan line f12, f13, f14 are each dynamically modified and set during the work depending on the current position of the work target point F on the spiral arm in order to produce the lenticule 21 with spiral-arm-shaped work trajectories or cut trajectories, the width of which proceeding from the peripheral edge 21r of the lenticule 21 reduces towards the centre point on the optical axis of the eye 2, or the width of which increases again from the centre point towards the peripheral edge 21r.

In the cut implementation according to FIG. 10, the scan lines overlaid on the work lines s are in each case dynamically modified and set in respect of their alignment angle φ' to the work line s, their length t and their tilt angle β or their curvature during the work depending on the current position of the work target point F on the work line s in order to produce the lenticule 21 with a predetermined free-form for correcting a higher-order aberration.

In the cut implementation according to FIG. 12, the alignment angle φ' and the length of the scan line F12, F13, F14 are each dynamically modified and set depending on the current position of the work target point F on the spiral arm s1, s2 during the work, like in the example of FIG. 8, in order to produce the lenticule 21 with spiral-arm-shaped work trajectories or cut trajectories, the width of which proceeding from the peripheral edge 21r of the lenticule 21 reduces towards the centre point on the optical axis of the eye 2, or the width of which increases again from the centre point towards the peripheral edge 21r. However, in contrast to the illustrative example according to FIG. 8, the spiral-arm-shaped work lines s1, s2 are not guided up to the centre point on the optical axis of the eye 2 but are guided around the centre point, forming a round clear space M and maintaining a predetermined distance from the centre point, such that a spiral arm s1 proceeding from the peripheral edge 21r is guided up to the edge of the clear space M and is guided proceeding therefrom to the peripheral edge 21r of the lenticule 21 again as a spiral arm s2 (or vice versa). Here, the length of the scan lines overlaid on the spiral work lines are set in such a way at the edge of the clear space M that as few overlaps as possible are caused by the scan lines when working on the clear space M.

Figure 13:
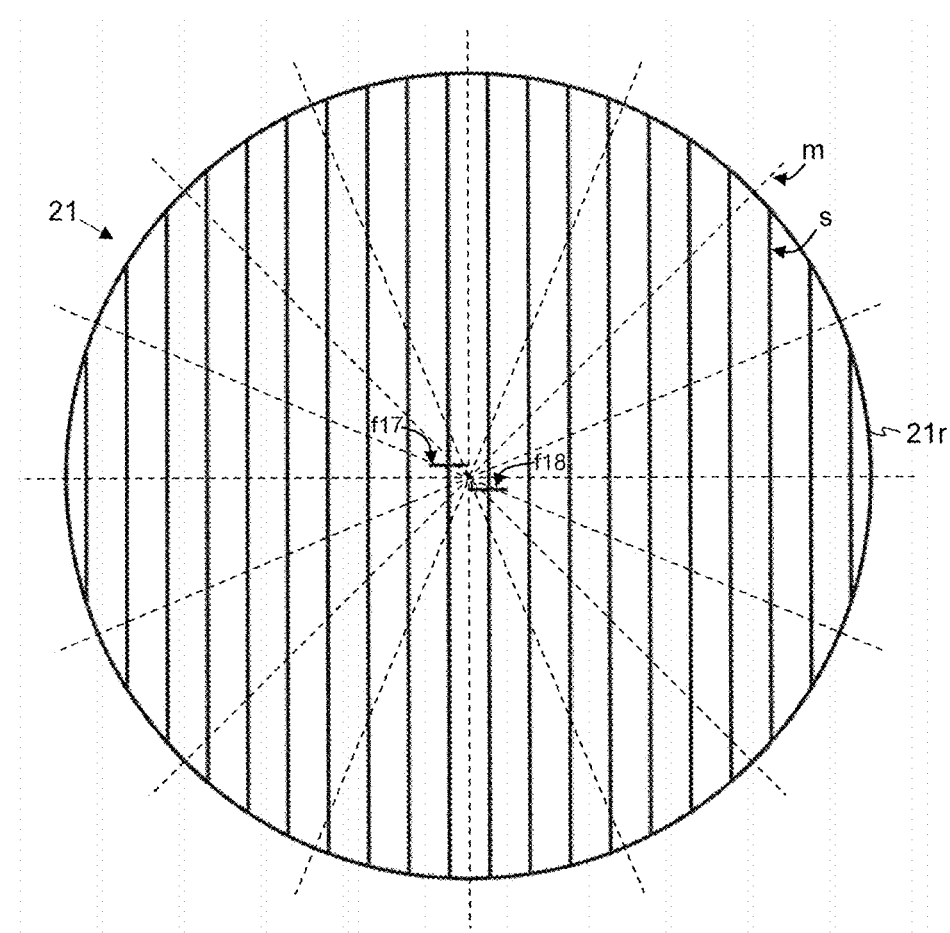
FIG. 13 shows a schematic plan view of a lenticule in the eye tissue, which is cut by a plurality of parallel work lines that extend across meridians of the lenticule and by scan lines extending thereacross.
Figure 14:
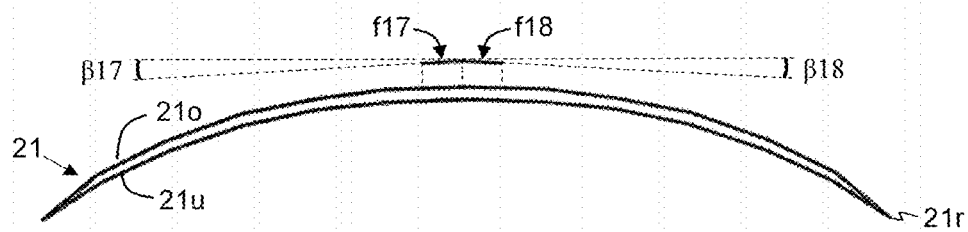
FIG. 14 shows a schematic cross-sectional view of a lenticule, which is cut by a plurality of parallel work lines that extend across meridians of the lenticule and by scan lines extending thereacross, wherein the scan lines of work lines extending next to one another are tilted differently in relation to a work plane that extends perpendicular to the plane of the drawing.

FIGS. 13 and 14 show a cut implementation with a plurality of work lines s that extend in planes extending parallel to the optical axis of the eye 2 and that each cut a plurality of meridians m of the lenticule 21. The scan lines f17, f18 overlaid on the work lines s are each aligned with an alignment angle φ' of 90°, i.e. normal to the relevant work line s. As schematically illustrated in the cross section in FIG. 14, the scan lines f17, f18 are each tilted out of the x/y-work plane with a tilt angle β17, β18 in order to adapt these to the curve of the upper and lower outer faces 21o, 21u, to be cut, of the lenticule 21.

Figure 11:
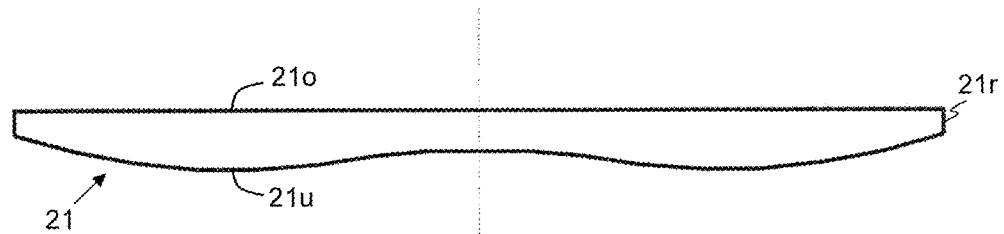
FIG. 11 shows a schematic cross-sectional view of a lenticule that is cut into the eye tissue of the cornea in the applanated state of the cornea for the purposes of correcting hyperopia.

FIG. 11 shows, in a cross section, a cut implementation of a lenticule 21 with an upper and lower outer face 21o, 21u and a peripheral edge 21r which, in the applanated state of the cornea, are cut into the eye tissue of the cornea 2 for the purposes of correcting hyperopia. The upper and lower outer face 21o, 21u of the lenticule 21 are cut using a cut implementation according to one of FIG. 5, 6, 7, 8, 9, 10, 12 or 14. The peripheral edge 21r is cut with a scan line that is tilted out of the x/y-work plane by 90°, said scan line being overlaid on a work line s that extends around the lenticule 21 to be cut in the peripheral edge 21r.

For better understanding, it should be noted here that the upper and lower outer face 21o, 21u of the lenticule 21 illustrated in FIG. 4 in cross-section, too, are cut in the non-applanated state of the cornea 2 with a cut implementation according to one of FIG. 5, 6, 7, 8, 9, 10, 12 or 13/14. The same applies to the cut methods explained below according to FIGS. 17 and 18.

In the following paragraphs, the implementation and production of an areal cut in the eye tissue 20, controlled by the circuit 10, and the cut implementation and production of a lenticule in the eye tissue 20, controlled by the circuit 10, are illustrated with reference to FIGS. 17 and 18.

In order to cut an area in the eye tissue 20, the circuit 10 controls the scanner system 100 and/or the optical functional modules thereof in order to guide the pulsed laser beam onto work target points F in the eye tissue 20. For the purposes of producing the cut area, the circuit 10 controls the scanner system 100 in step S1 in such a way that the pulsed laser beam scans the eye tissue 20 in work trajectories that extend parallel next to one another or that extend next to one another and have a spiral, circular or elliptical form. In the process, the second scanner module 15 of the scanner system 10 guides the pulsed laser beam in the feed direction v onto work target points F along a work line s and the first scanner module 12 of the scanner system 100 guides the pulsed laser beam onto work target points F along a scan line f that extends across the work line s, as illustrated in FIGS. 2a, 2b and 4-14 and as described above with reference to these figures, and so a cut trajectory defined by the work trajectory is produced in step S11.

Figure 15:
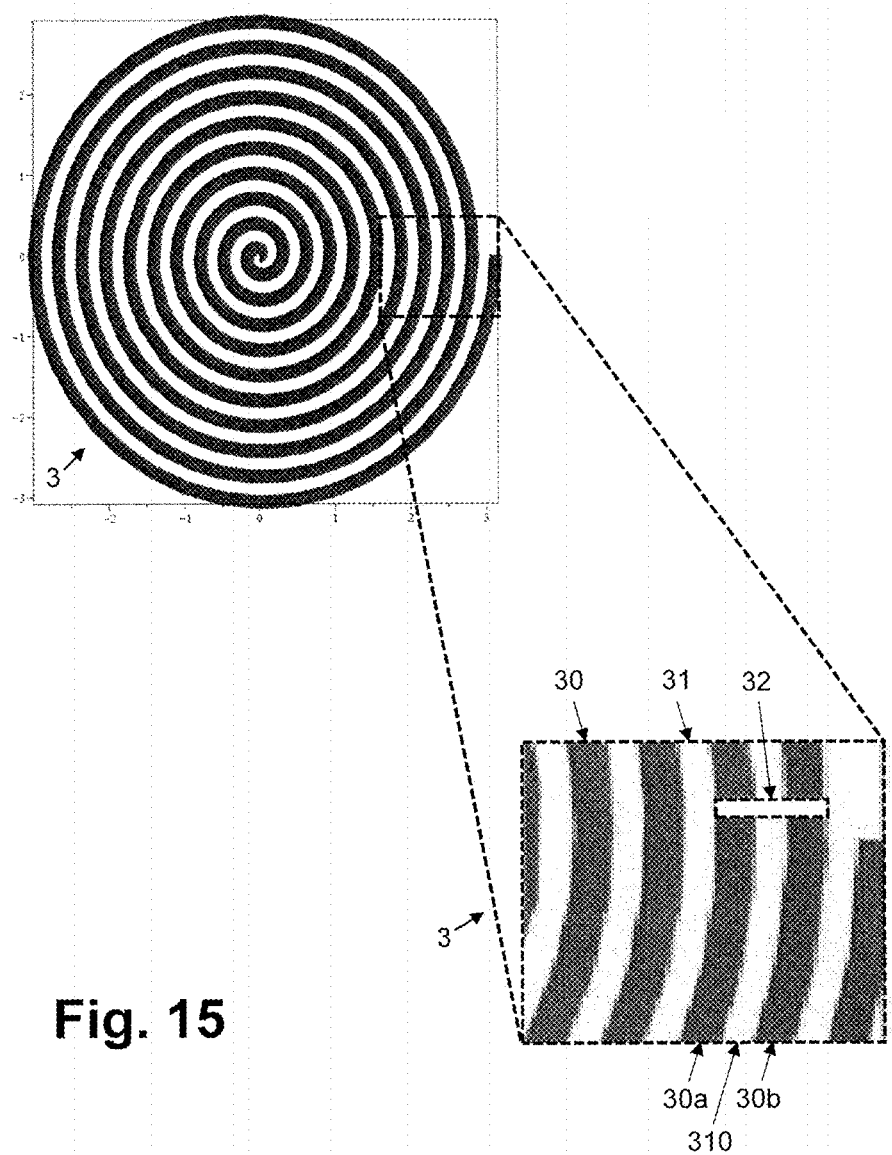
FIG. 15 shows a schematic view of cut trajectories of a lenticule, extending next to one another, which are separated by remaining tissue bridges in the eye tissue, which are cut by a spiral elliptical work line and by scan lines extending thereacross.

In step S11, the circuit 10 controls the scanner system 100 and/or the optical functional modules thereof in such a way that the cut trajectories are produced in a plurality of work trajectories, wherein tissue bridges that remain in each case are left between the cut trajectories. This is illustrated in FIG. 15 using the example of spiral work lines and spiral work trajectories and the resultant cut trajectory 30 defined thereby. The work trajectories 3 extending next to one another are visible in the upper part of FIG. 15. As is visible in a section illustrated with magnification in the lower part of FIG. 15, the work trajectories 3 extending next to one another are worked on in step S11 in such a way that cut trajectories 30 are produced in the worked-on work trajectories, said cut trajectories being separated by tissue bridges 31 in interposed, not yet worked on work trajectories. Depending on the form of the work line s, the work trajectories 3 and/or cut trajectories 30, based thereon, extend parallel next to one another or extend next to one another in a spiral, circular or elliptical fashion, or in free-form closed curves.

In optional step S12, the circuit 10 controls the measurement system 17 in such a way that the latter captures the produced cut trajectories 30 and determines the remaining tissue bridges 31 on the basis of the produced cut trajectories 30. On account of the determined tissue bridges 31, the circuit 10 determines the not treated work trajectories yet to be treated. In FIG. 15, reference sign 32 relates to a captured portion of the produced cut trajectories 30a, 30b for determining the interposed tissue bridge 310 and the yet to be worked on corresponding work trajectory. In the case of the measurement system 17 embodied as an interferometric measurement system, in particular, the capture of the produced cut trajectories 30a, 30b and the determination of the interposed tissue bridge 310 for positioning the work trajectory to be worked on is carried out continuously during the work ("online"), and so the current work target point F of the work line s or of the scan line f aligned thereacross, in the work direction v, follows ("upstream") the captured portion 32 ("downstream") of the produced cut trajectories 30a, 30b.

In step S13, the circuit 10 controls the scanner system 100 and/or the optical functional modules thereof in such a way that the specific tissue bridges 31 or the yet to be treated work trajectories are worked on. Expressed differently, the scanner system 100 is controlled in such a way that it guides the pulsed laser beam onto work target points F into the tissue bridges 31 remaining between the cut trajectories 30 in order to complete the tissue cut. In one illustrative example variant, the tissue bridges are worked on in work trajectories 3, the width of which goes beyond the width of the specific tissue bridges 31. Once all remaining tissue bridges 31 have been worked on, the area is completely cut and the corresponding cut area is produced in the eye tissue 20.

Two cut areas, the lower outer face 21u and the upper outer face 21o of the lenticule 21 are cut in the eye tissue for the purposes of cutting a lenticule 21.

Figure 17:
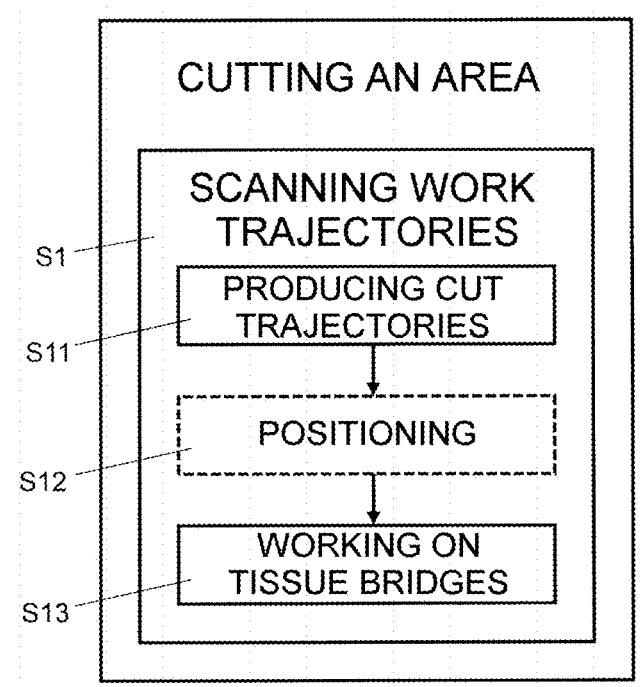
FIG. 17 shows a flowchart that illustrates carrying out and producing an areal cut in the eye tissue.
Figure 18:
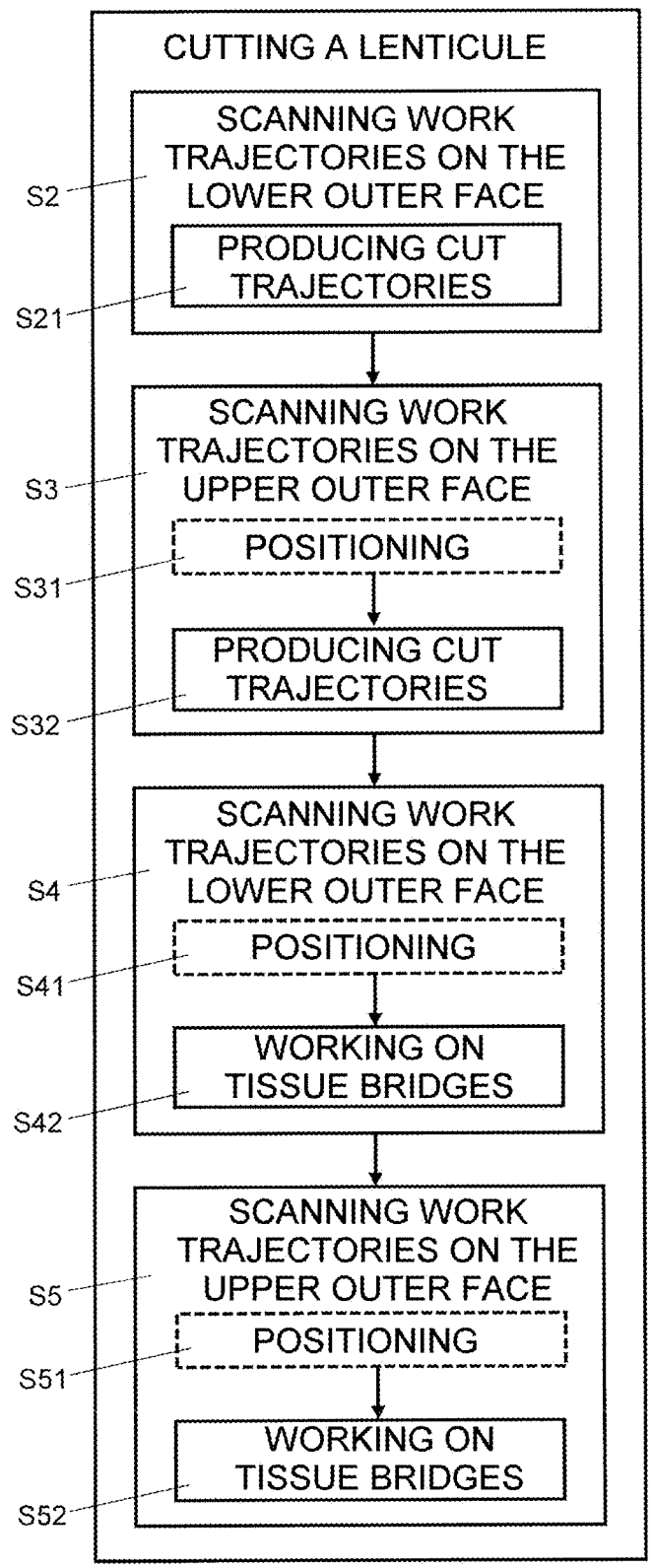
FIG. 18 shows a flowchart that illustrates carrying out the cut and producing a lenticule in the eye tissue.

FIG. 18 illustrates a cut method in which a lenticule 21 in the eye tissue 20 is cut in a sequence of cut sequences. Here, the circuit 10 controls the scanner system 100 and/or the optical functional modules thereof in such a way that, in step S2, the work trajectories 30 on the lower outer face 21u of the lenticule 21 to be cut are worked on and, in step S21, the cut trajectories 30 with remaining tissue bridges 31 are produced, as described above with respect to FIG. 17 in conjunction with steps S1 and S11. Expressed differently, the lower outer face 21u of the lenticule 21 is initially cut incompletely in steps S2, S21 with remaining tissue bridges 31 between the cut trajectories 30.

In contrast to cutting the cut area according to FIG. 17, cutting the upper outer face 21o of the lenticule 21 is started first in the subsequent step S3. Here, the circuit 10 controls the scanner system 100 and/or the optical functional modules thereof in such a way that, in step S3, the work trajectories 30 on the upper outer face 21o of the lenticule 21 to be cut are worked on. To this end, in optional step S31, the circuit 10 controls the measurement system 17 in such a way that the latter captures the cut trajectories 30 on the lower outer face 21u that were produced in step S2 and/or S21 and determines the work trajectories 3 to be worked on or the cut trajectories 30 to be cut on the upper outer face 21o on the basis of the produced cut trajectories 30 of the lower outer face 21u. Here, in addition to the lateral positioning of the upper outer face 21o with respect to the lower outer face 21u, a predetermined centre thickness d and/or a predetermined thickness profile D of the lenticule 21 to be cut is also observed. In one illustrative example variant, the circuit 10 moreover controls the measurement system 17 in such a way that the measurement system 17 captures deformations in the eye tissue that were caused by gas bubbles produced when cutting the cut trajectories 30 on the lower outer face 21u, and the upper outer face 21o, or the work trajectories 3 to be worked on and, as a result thereof, cut trajectories 30 to be cut on the upper outer face 21o are positioned taking account of the captured deformations in respect of the captured lower outer face 21u. Then, the circuit 10 controls the scanner system 100 and/or the optical functional modules thereof in such a way that, in step S32, the cut trajectories 30 are produced with remaining tissue bridges 31 on the upper outer face 21o, as described above with reference to FIG. 17 in conjunction with steps S1 and S11. In one illustrative example variant, the circuit 10 determines the work trajectories 3 for producing the cut trajectories 30 on the upper outer face 21o with a smaller trajectory width in respect of the captured cut trajectories 30 on the lower outer face 21u. In step S32, the upper outer face 21o of the lenticule 21 is also cut in incomplete fashion with remaining tissue bridges 31 between the cut trajectories 30.

In subsequent step S4, the tissue bridges 31 remaining on the lower outer face 21u between the cut trajectories 30 are cut. To this end, the circuit 10 controls the scanner system 100 and/or the optical functional modules thereof in such a way that, in step S4, the work trajectories 30 with the remaining tissue bridges 31 on the lower outer face 21u of the lenticule 21 to be cut are worked on. In optional step S41, the circuit 10 controls the measurement system 17 in such a way that the latter captures the already produced cut trajectories 30 on the lower outer face 21u and determines the remaining tissue bridges 31 on the basis of the captured cut trajectories 30. On account of the determined tissue bridges 31, the circuit 10 determines on the lower outer face 21u the not treated work trajectories yet to be treated. In step S42, the circuit 10 controls the scanner system 100 and/or the optical functional modules thereof in such a way that the remaining tissue bridges 31 or the yet to be treated work trajectories are worked on and cut as a result thereof, as described above with respect to FIG. 17 in conjunction with step S13, and, as result thereof, completes the tissue cut on the lower outer face 21u of the lenticule 21.

In subsequent step S5, the tissue bridges 31 remaining on the upper outer face 210 between the cut trajectories 30 are cut. To this end, the circuit 10 controls the scanner system 100 and/or the optical functional modules thereof in such a way that, in step S5, the work trajectories 30 with the remaining tissue bridges 31 on the upper outer face 210 of the lenticule 21 to be cut are worked on. In optional step S51, the circuit 10 controls the measurement system 17 in such a way that the latter captures the already produced cut trajectories 30 on the upper outer face 210 and determines the remaining tissue bridges 31 on the basis of the captured cut trajectories 30. On account of the determined tissue bridges 31, the circuit 10 determines on the upper outer face 210 the not treated work trajectories yet to be treated. In step S52, the circuit 10 controls the scanner system 100 and/or the optical functional modules thereof in such a way that the remaining tissue bridges 31 or the yet to be treated work trajectories are worked on, as described above with respect to FIG. 17 in conjunction with step S13, and, as result thereof, completes the tissue cut on the upper outer face 210 of the lenticule 21, as a result of which the lenticule 21 is completely cut.

What is claimed is:

1. An ophthalmological apparatus for working on eye tissue, comprising:
   a laser source configured to produce a pulsed laser beam;
   a focusing optical unit configured to focus the pulsed laser beam into the eye tissue;
   a scanner system, comprising a first scanner module and a second scanner module, for deflecting the pulsed laser beam onto work target points in the eye tissue;
   a circuit for controlling the ophthalmological apparatus, wherein the circuit is configured to control the second scanner module in such a way that the second scanner module guides the pulsed laser beam in a feed direction onto work target points along a work line that extends along an outer face of a lenticule to be cut in the eye tissue,
   wherein the first scanner module is configured to guide the pulsed laser beam onto work target points, along a scan line that extends across the work line, with a substantially higher scanning speed in comparison with a scanning speed of the second scanner module in the feed direction; and
   wherein the circuit is configured to control the scanner system to cut the lenticule in the eye tissue by:
      working initially a work trajectory on a lower outer face of the lenticule,
      working subsequently, when the lower outer face of the lenticule is yet cut incompletely, a work trajectory on an upper outer face of the lenticule,
      working subsequently, when the upper outer face of the lenticule is yet cut incompletely, a yet to be treated work trajectory on the lower outer face of the lenticule, and
      working subsequently a yet to be treated work trajectory on the upper outer face of the lenticule.

2. The ophthalmological apparatus of claim 1, wherein the first scanner module is configured to guide the pulsed laser beam onto work target points along the scan line that extends across the work line at an alignment angle in a work plane; and the ophthalmological apparatus further comprises a z-modulator configured to tilt the scan line out of the work plane depending on a specific work target point of the second scanner module on the work line such that the scan line runs substantially along the outer face of the lenticule.

3. The ophthalmological apparatus of claim 2, wherein the z-modulator is further configured to bend the scan line in relation to the work plane, wherein the circuit is further configured to control the z-modulator depending on the specific work target point of the second scanner module on the work line in such a way that the z-modulator bends the scan line depending on the specific work target point of the second scanner module on the work line for adaptation to the outer face of the lenticule.

4. The ophthalmological apparatus of claim 2, further comprising:
   a rotator configured to rotate a fast scan plane defined by the scan line and the pulsed laser beam about an optical transmission axis in order to modify the alignment angle of the scan line in relation to the work line; the z-modulator is configured to bend the scan line in relation to the work plane; and
   a scan length modulator configured to modify a length of the scan line,
   wherein the circuit is further configured, depending on the specific work target point of the second scanner module on the work line, to control the rotator to set the alignment angle of the scan line in relation to the work line, to control the z-modulator to bend the scan line in relation to the work plane and to control the scan length modulator to set the length of the scan line in such a way that the outer face of the lenticule is cut in a predetermined free-form for correcting a higher-order aberration.

5. The ophthalmological apparatus of claim 2, further comprising:
   a rotator configured to rotate a fast scan plane defined by the scan line and the pulsed laser beam about an optical transmission axis in order to modify the alignment angle of the scan line in relation to the work line; and
   a scan length modulator configured to modify a length of the scan line,
   wherein the circuit is further configured, depending on the specific work target point of the second scanner module on the work line, to control the rotator to set the alignment angle of the scan line in relation to the work line, to control the z-modulator to tilt the scan line in relation to the work plane and to control the scan length modulator to set the length of the scan line in such a way that the outer face of the lenticule is cut in a predetermined free-form for correcting a higher-order aberration.

6. The ophthalmological apparatus of claim 1, further comprising a rotator configured to rotate a fast scan plane defined by the scan line and the pulsed laser beam about an optical transmission axis in such a way that an alignment angle of the scan line is modified in relation to the work line.

7. The ophthalmological apparatus of claim 6, wherein the circuit further is configured to control the rotator depending on a specific work target point of the second scanner module on the work line such that an alignment angle of the scan line relative to the work line is set depending on the specific work target point of the second scanner module on the work line.

8. The ophthalmological apparatus of claim 1, further comprising a scan length modulator configured to modify a length of the scan line, wherein the circuit is further configured to control the scan length modulator depending on a specific work target point of the second scanner module on the work line such that the length of the scan line is set depending on the specific work target point of the second scanner module on the work line.

9. The ophthalmological apparatus of claim 1, wherein the circuit is further configured to control the second scanner module in such a way that the second scanner module guides the pulsed laser beam onto work target points in a work plane along a circular or elliptical work line that extends along the outer face of the lenticule.

10. The ophthalmological apparatus of claim 1, wherein the circuit is further configured to control the second scanner module in such a way that the second scanner module guides the pulsed laser beam onto work target points along a spiral work line that extends along the outer face of the lenticule.

11. The ophthalmological apparatus of claim 1, wherein the circuit is further configured to control the second scanner module in such a way that the second scanner module guides the pulsed laser beam onto work target points along a work line that extends along the outer face of the lenticule in one of: a circular arc segment, a spiral arc segment, or a curved line segment.

12. The ophthalmological apparatus of claim 1, wherein the circuit is further configured to control the second scanner module in such a way that the second scanner module guides the pulsed laser beam onto work target points along a plurality of spiral work lines, said plurality of spiral work lines extending in a spiral arm shape in a direction of a centre of the outer face proceeding from a periphery of the outer face of the lenticule in a first step, and extending in a spiral arm shape to the periphery of the outer face of the lenticule proceeding from the centre in a second step.

13. The ophthalmological apparatus of claim 1, wherein the circuit is further configured to control the second scanner module in such a way that the second scanner module guides the pulsed laser beam onto work target points along a plurality of spiral work lines, said plurality of work lines extending in a spiral arm shape in a direction of a centre of the outer face proceeding from a periphery of the outer face of the lenticule and ending at a specific distance from the centre in a first step, and extending in a spiral arm shape to the periphery of the outer face of the lenticule proceeding from the specific distance from the centre in a second step, or conversely, extending in a spiral arm shape to the periphery of the outer face of the lenticule proceeding from the specific distance from the centre in a first step and extending in a spiral arm shape in the direction of the centre of the outer face from the periphery of the outer face of the lenticule.

14. The ophthalmological apparatus of claim 1, wherein the circuit is further configured to control the second scanner module in such a way that the second scanner module guides the pulsed laser beam in the feed direction onto work target points along a work line that extends along an outer face of a lenticule to be cut in the eye tissue, transversely to meridians of the lenticule.

15. The ophthalmological apparatus of claim 1, wherein the circuit is further configured to control the scanner system to cut the lenticule in the eye tissue by working repeatedly and alternately first a work trajectory on the lower outer face of the lenticule and then a work trajectory on the upper outer face of the lenticule, until the lenticule is cut completely in the eye tissue.

16. The ophthalmological apparatus of claim 1, wherein the ophthalmological apparatus further comprises a measurement system configured to optically capture structures in the eye tissue; and the circuit is configured to control the measurement system to capture trajectories cut on the lower outer face of the lenticule, and to position, with respect to the captured trajectories cut on the lower outer face of the lenticule, work trajectories to be treated on the upper outer face of the lenticule.

17. A method comprising:
producing, by a laser source, a pulsed laser beam;
focusing, by a focusing optical unit, the pulsed laser beam into eye tissue;
deflecting, by a scanner system comprising a first scanner module and a second scanner module, the pulsed laser beam onto work target points in the eye tissue;
controlling, by a circuit, the second scanner module to guide the pulsed laser beam in a feed direction onto work target points along a work line that extends along an outer face of a lenticule to be cut in the eye tissue;
controlling, by the circuit, the first scanner module to guide the pulsed laser beam onto work target points along a scan line that extends across the work line, with a substantially higher scanning speed in comparison with a scanning speed of the second scanner module in the feed direction; and
controlling, by the circuit, the scanner system to cut the lenticule in the eye tissue by:
working initially a work trajectory on a lower outer face of the lenticule,
working subsequently, when the lower outer face of the lenticule is yet cut incompletely, a work trajectory on an upper outer face of the lenticule,
working subsequently, when the upper outer face of the lenticule is yet cut incompletely, a yet to be treated work trajectory on the lower outer face of the lenticule, and
working subsequently a yet to be treated work trajectory on the upper outer face of the lenticule.

18. The method of claim 17, wherein the circuit controls the first scanner module to guide the pulsed laser beam onto work target points along a scan line that extends across the work line at an alignment angle in a work plane; and the method further comprises tilting, by a z-modulator, the scan line out of the work plane, depending on a specific work target point of the second scanner module on the work line, such that the scan line runs substantially along the outer face of the lenticule.

19. The method of claim 17, wherein the circuit controls the scanner system to cut the lenticule in the eye tissue by working repeatedly and alternately first a work trajectory on the lower outer face of the lenticule and then a work trajectory on the upper outer face of the lenticule, until the lenticule is cut completely in the eye tissue.

20. The method of claim 17, wherein the method further comprises the circuit controlling a measurement system to capture trajectories cut on the lower outer face of the lenticule, and to position, with respect to the captured trajectories cut on the lower outer face of the lenticule, work trajectories to be treated on the upper outer face of the lenticule.

* * * * *